United States Patent
Akingba et al.

(10) Patent No.: US 10,413,395 B2
(45) Date of Patent: Sep. 17, 2019

(54) MODULAR STENT GRAFTING METHODS AND APPARATUS

(71) Applicant: INDIANA UNIVERSITY RESEARCH AND TECHNOLOGY CORPORATION, Indianapolis, IN (US)

(72) Inventors: A. George Akingba, Carmel, IN (US); Raghu L. Motaganahalli, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 640 days.

(21) Appl. No.: 14/228,414

(22) Filed: Mar. 28, 2014

(65) Prior Publication Data

US 2014/0296963 A1    Oct. 2, 2014

Related U.S. Application Data

(60) Provisional application No. 61/806,161, filed on Mar. 28, 2013.

(51) Int. Cl.
| | | |
|---|---|---|
| *A61F 2/07* | (2013.01) | |
| *A61F 2/852* | (2013.01) | |
| *A61F 2/82* | (2013.01) | |
| *A61F 2/06* | (2013.01) | |

(52) U.S. Cl.
CPC ............... *A61F 2/07* (2013.01); *A61F 2/852* (2013.01); *A61F 2002/061* (2013.01); *A61F 2002/067* (2013.01); *A61F 2002/821* (2013.01); *A61F 2002/826* (2013.01); *A61F 2250/0006* (2013.01); *A61F 2250/0062* (2013.01)

(58) Field of Classification Search
CPC .................. A61F 2/07; A61F 2002/065; A61F 2002/821; A61F 2002/823; A61F 2002/826; A61F 2/852; A61F 2/856; A61F 2002/067
USPC ........................................................ 623/1.35
See application file for complete search history.

(56) References Cited

U.S. PATENT DOCUMENTS

| | | | |
|---|---|---|---|
| 7,850,725 B2 | 12/2010 | Vardi et al. | |
| 7,955,374 B2 | 6/2011 | Erickson et al. | |
| 8,414,639 B2 | 4/2013 | Tischler | |
| 2004/0215327 A1* | 10/2004 | Doig et al. ................ | A61F 2/07 623/1.16 |

(Continued)

*Primary Examiner* — Suba Ganesan
(74) *Attorney, Agent, or Firm* — Barnes & Thornburg LLP

(57) ABSTRACT

The present disclosure provides a modular stent assembly for deployment within a lumen. The assembly may include primary and secondary stent portions. Each stent portion includes a sheet having an incomplete annular profile. The sheet includes a graft material disposed on a wire matrix. Each stent portion further includes an aperture positioned in the sheet, and first and second side walls. The first side wall extends between the aperture and a first longitudinal edge of the sheet. The second side wall extends between the aperture and a second longitudinal edge of the sheet, which is spaced apart from the first edge. The stent portions mate to define an interior space in which is positioned an expandable securement stent. An outer wall of the securement stent is sized to compress the side walls of the stent portions between the body of the securement stent and a wall defining the lumen.

9 Claims, 19 Drawing Sheets

(56) References Cited

U.S. PATENT DOCUMENTS

| | | |
|---|---|---|
| 2004/0254634 A1 | 12/2004 | Verlee et al. |
| 2006/0247760 A1 | 11/2006 | Ganesan et al. |
| 2007/0055362 A1* | 3/2007 | Brown ................... A61F 2/91 623/1.35 |
| 2007/0168016 A1 | 7/2007 | Gronemeyer et al. |
| 2007/0173921 A1* | 7/2007 | Wholey ................. A61F 2/915 623/1.15 |
| 2008/0114444 A1* | 5/2008 | Yu ........................... A61F 2/07 623/1.13 |
| 2013/0218259 A1 | 8/2013 | Quinn |

\* cited by examiner

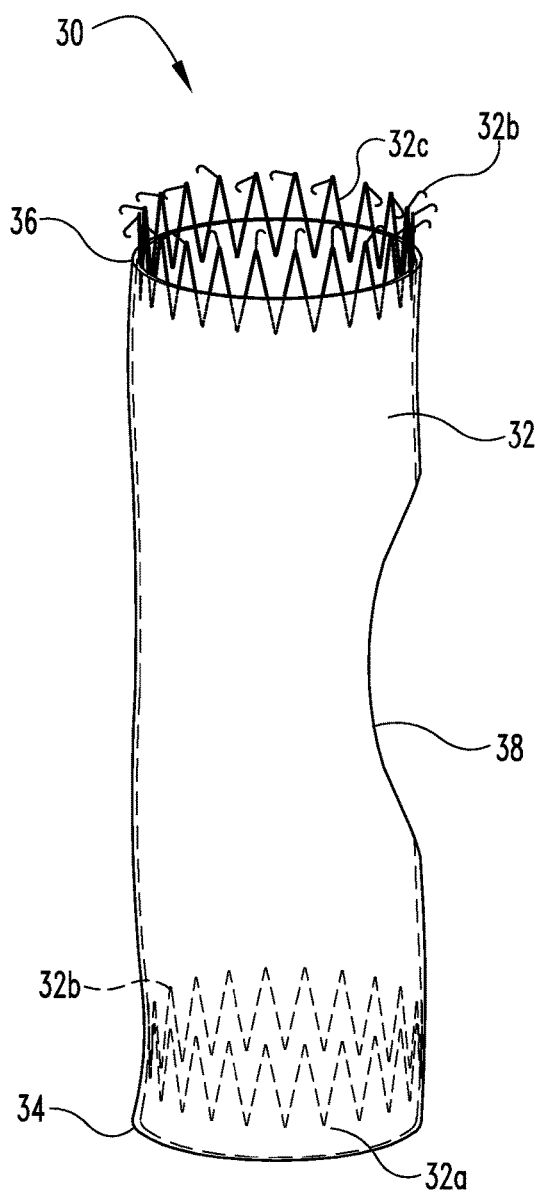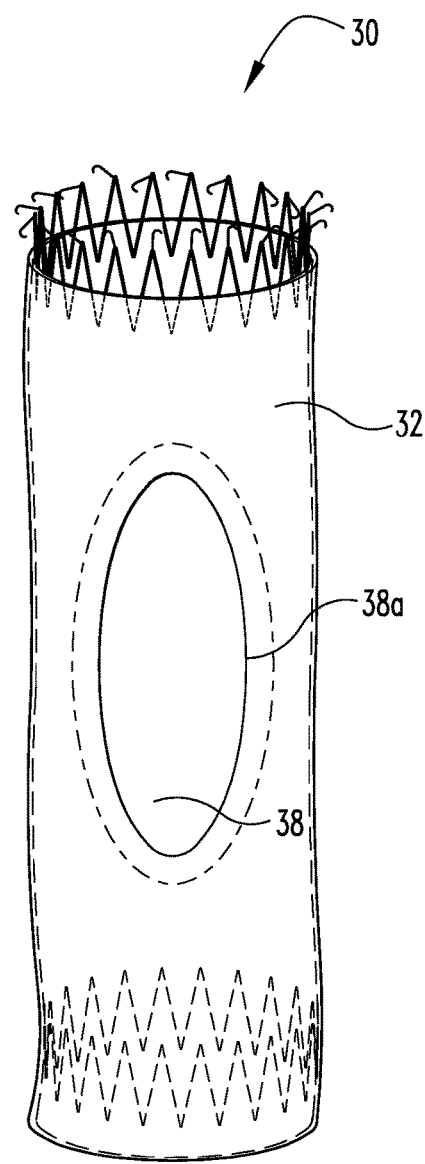
Fig. 1a  Fig. 1b

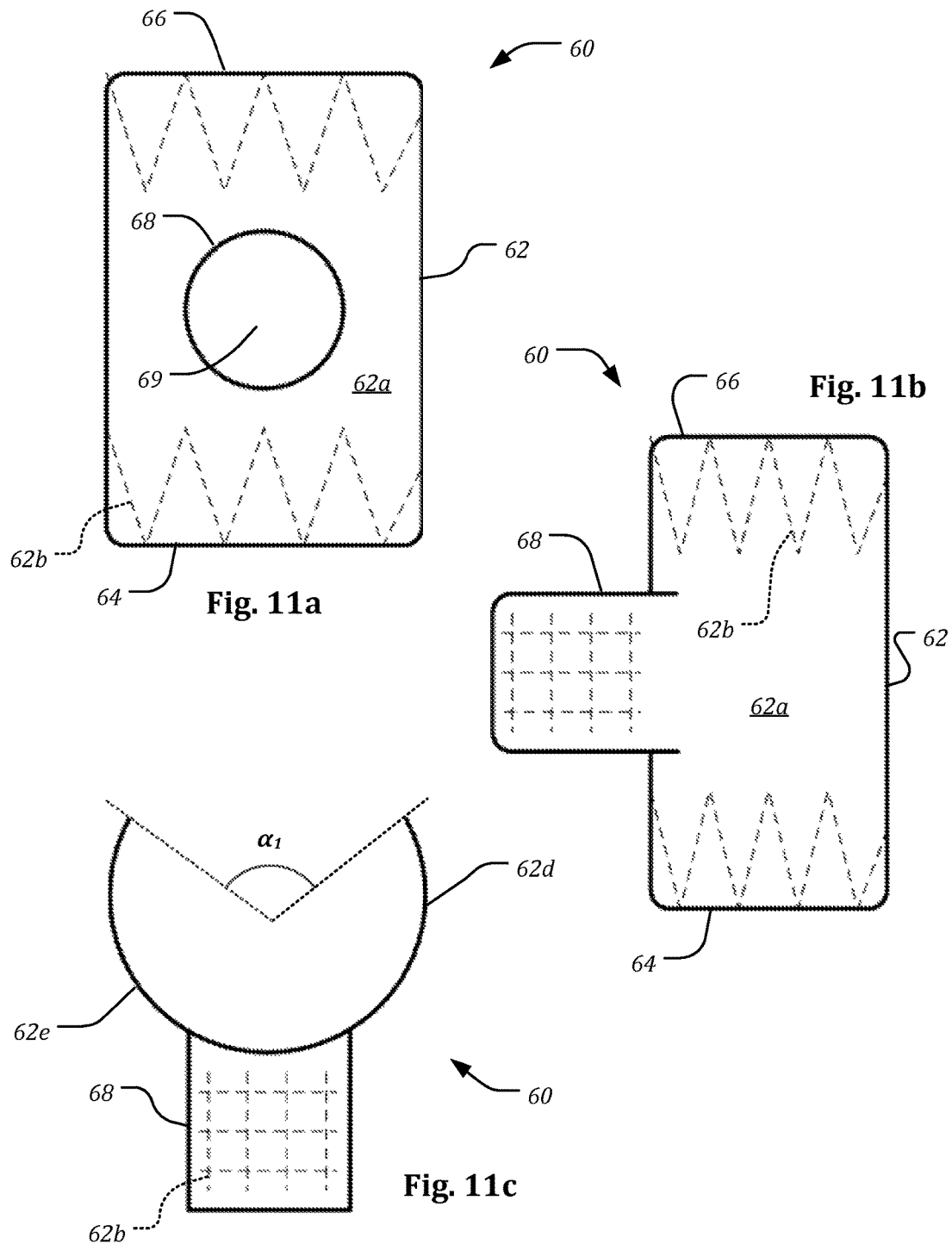

MODULAR STENT GRAFTING METHODS AND APPARATUS

CROSS-REFERENCE TO RELATED APPLICATIONS

This application claims the benefit of U.S. Provisional Patent Application Ser. No. 61/806,161 filed on Mar. 28, 2013.

STATEMENT REGARDING FEDERALLY SPONSORED RESEARCH

Not applicable.

BACKGROUND OF THE INVENTION

The field of the disclosure relates to apparatus for use in treating arterial or vascular disease. More particularly, the disclosure relates to a modular stent assembly for the treatment at the intersection of one or more arterial or vascular passages, with various embodiments of the present invention pertaining to the assembly of multiple stents and modular stents.

Various methods are available for the treatment of arterial diseases such as aneurysms located within the thoracic and abdominal aorta. While invasive surgeries may be carried out to directly treat the aneurysm, other non-invasive techniques may be used. For example, an endovascular stent may be deployed in the lumen near the location of the aneurysm through endoscopic surgery or another suitable technique. Stents are normally delivered into the lumen to be treated in a collapsed state with a diameter or crossing profile that is smaller than the diameter of the lumen. The stent grafts are then expanded with an expanding member, such as a balloon catheter, or are released from a constrained configuration and self-expanded by nature of their construction.

While a number of types of endovascular stents have been conceived, there is still a need for new and improved designs. In one aspect, there is a need for a stent or stent assembly that can be deployed at the intersection of one or more arterial passages. In another aspect, there is a need for a set of modular stents that may be adjusted or assembled in myriad ways to accommodate various geometries and angles within an arterial space.

SUMMARY OF THE INVENTION

The present invention overcomes the aforementioned drawbacks by providing a modular stent assembly. According to one aspect of the present disclosure, a modular stent assembly for deployment within a lumen is provided. The modular stent assembly includes a trunk stent with an expandable body defining an interior space, the body extending between an open proximal end and an open distal end. The trunk stent further includes a graft material disposed on the body, and an aperture positioned between the proximal end and the distal end, the aperture being formed through the body and the graft material. The assembly further includes a trumpet stent with an expandable body extending between an open first end and an open second end, an outer perimeter of the first end being greater than an outer perimeter of the second end. A graft material is disposed on the body of the trumpet stent. The assembly further includes a securement stent with an expandable body extending between an open proximal end and an open distal end of the securement stent. The body of the trumpet stent passes through the aperture of the trunk stent, the first end of the trumpet stent positioned at least partially within the interior space of the trunk stent. The securement stent is positioned within the interior space of the trunk stent. An outer wall of the securement stent contacts an inner wall of the trunk stent and the first end of the trumpet stent, thereby coupling the trumpet stent to the trunk stent.

In one aspect, at least one of the trunk stent, the trumpet stent and the securement stent includes a biocompatible, shape-memory material. In another aspect, the material is selected from nitinol and stainless steel. In yet another aspect, the second end of the trumpet stent is in fluid communication with the proximal end and the distal end of the trunk stent. In still another aspect, the expandable body of at least one of the trunk stent, the trumpet stent and the securement stent is balloon expandable. In another aspect, expandable body of at least one of the trunk stent, the trumpet stent and the securement stent is self-expanding.

In a further aspect, at least a portion of the graft material disposed on the body of the trunk stent extends partially over the aperture in the body of the trunk stent. In one aspect, at least a portion of the graft material disposed on the body of the trumpet stent extends partially past the first end of the body of the trumpet stent. In another aspect, the modular stent assembly may further include at least two trumpet stents. The body of each of the trumpet stents passes through the aperture of the trunk stent, the first ends of each of the trumpet stents positioned at least partially within the interior space of the trunk stent.

According to another aspect of the present disclosure, a modular stent assembly for deployment within a lumen is provided. The modular stent assembly includes a primary stent portion and a secondary stent portion, each of the primary and secondary stent portions with a sheet including a graft material disposed on a wire matrix, the sheet having an incomplete annular profile. The stent portions further include an aperture positioned in the sheet, a first side wall extending between the aperture and a first longitudinal edge of the sheet, and a second wall extending between the aperture and a second longitudinal edge of the sheet, the second edge being spaced apart from the first edge. The primary stent portion is mated with the secondary stent portion, thereby defining an interior space. Moreover, the first wall of the primary stent portion at least partially overlaps the first wall of the secondary stent portion, and the second wall of the primary stent portion at least partially overlaps the second wall of the secondary stent portion. The assembly also includes a securement stent positioned in the interior space. The securement stent includes an expandable body extending between a proximal end and a distal end of the securement stent. An outer wall of the securement stent is sized to compress the walls of the primary and secondary stent portions between the body of the securement stent and a wall defining the lumen.

In one aspect, at least one of the primary stent portion, the secondary stent portion, and the securement stent includes a biocompatible, shape-memory material. The material is selected from nitinol and stainless steel. In another aspect, the aperture of primary stent portion, the aperture of the secondary stent portion, and first end and second end of the securement stent are in fluid communication. In yet another aspect, the expandable body of the securement stent is balloon expandable. In still another aspect, the expandable body of the securement stent is self-expanding.

In one aspect, at least one of the primary stent portion and the secondary stent portion further includes a branch portion with a first open end, a second open end, and an expandable body extending therebetween. The first end is disposed about and extending from the aperture in the sheet. In another aspect, for at least one of the primary stent portion and the secondary stent portions, the width of the first wall is greater than the width of the second wall. In yet another aspect, for at least one of the primary stent portion and the secondary stent portions, the width of the first wall is equal to the width of the second wall.

In one aspect, each of the primary and secondary stent portions includes a proximal end and a distal end. The proximal end of the primary stent portion is offset from the proximal end of the secondary stent portion. In a further aspect, an angle between the aperture of the primary stent portion and the aperture of the secondary stent portion is less than 180 degrees.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1a is side perspective view of a trunk stent according to one embodiment of the present disclosure;

FIG. 1b is a front perspective view thereof;

FIG. 11a front elevational schematic representation of a modular open body stent according to one embodiment of the present disclosure;

FIG. 11b is a side elevational view thereof;

FIG. 11c is a top plan view thereof;

FIG. 13 is a schematic cutaway representation of a region of the lower aorta including an abdominal aortic aneurism and an installed primary stent portion such as the one shown in FIG. 11a;

FIG. 14 is a schematic cutaway representation of the abdominal aorta of FIG. 13 further including an installed secondary stent portion such as the one shown in FIG. 11a;

FIG. 18b is a cross-sectional view of the modular stent assembly of FIG. 18a as taken along line 18b-18b of FIG. 18a;

Like reference numerals will be used to refer to like parts from figure to figure in the following detailed description.

DETAILED DESCRIPTION OF THE INVENTION

Figure 2A:
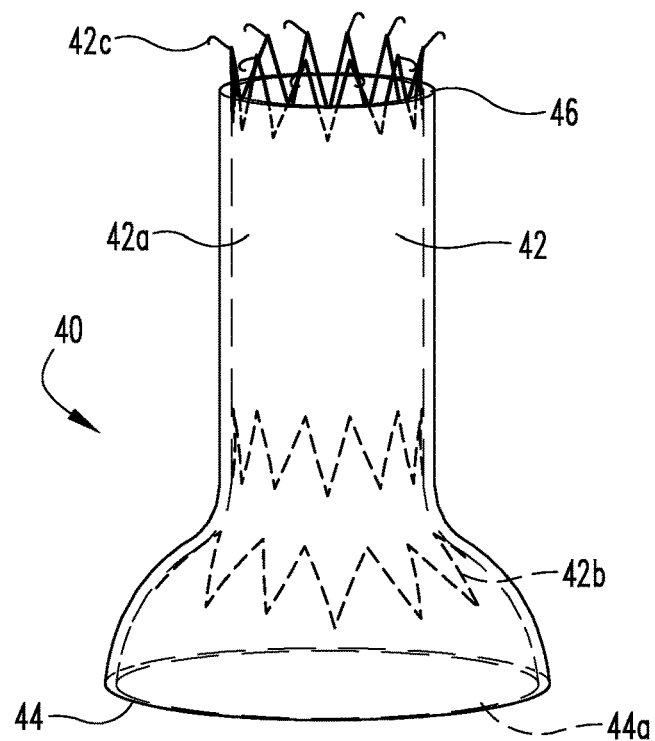
FIG. 2a is a side perspective view of a trumpet stent according to one embodiment of the present disclosure.

The present disclosure has been described in terms of one or more preferred embodiments, and it should be appreciated that many equivalents, alternatives, variations, and modifications, aside from those expressly stated, are possible and within the scope of the disclosure.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates. At least one embodiment of the present disclosure will be described and shown, and this application may show or describe other embodiments of the present disclosure. It is understood that any reference to "the disclosure" is a reference to an embodiment of a family of disclosures, with no single embodiment including an apparatus, process, or composition that should be included in all embodiments, unless otherwise stated. Further, although there may be discussion with regards to "advantages" provided by some embodiments of the present disclosure, it is understood that yet other embodiments may not include those same advantages, or may include yet different advantages. Any advantages described herein are not to be construed as limiting to any of the claims.

The use of an N-series prefix for an element number (NXX) refers to an element that is the same as the non-prefixed element (XX), except as shown and described thereafter. As an example, an element 120 would be the same as element 20, except for those different features of element 120 shown and described. Further, common elements and common features of related elements are drawn in the same manner in different figures, and/or use the same symbology in different figures. As such, it is not necessary to describe the features of 120 and 20 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

FIGS. 1a and 1b show side and frontal views, respectively, of a generally cylindrical trunk stent 30 according to one embodiment of the present disclosure. Trunk stent 30 includes a body 32 extending from a proximal end 34 to a distal end 36 (the terms proximal and distal refer to the location of that end of the stent relative to the handle of the instrument that the surgeon is using to implant the stent). In some embodiments, body 32 has an annular or cylindrical shape defining an interior space with open proximal and distal ends. Stent body 32 includes a graft material 32a that is disposed on or covers and is attached to a wire matrix 32b. Wire matrix 32b may be fabricated from a biocompatible, shape-memory material. In one aspect, the wire matrix 32b may be a metal such as stainless steel, nitinol (NiTi) and tantalum (Ta). In another aspect, the wire matrix may be an alloy such as iron platinum, iron palladium, iron nickel cobalt titanium, iron nickel carbon, iron manganese silicon, and iron manganese silicon chromium nickel. In still another aspect, a biocompatible polymeric material may be used such as polyethylene or another non-degradable polymeric material. The diameter of the metal or polymeric wire used for construction of the wire matrix may be between about 0.005 inches to about 0.02 inches. Other wire matrices or expandable materials described herein may similarly include one of the aforementioned materials described with respect to wire matrix 32b.

The graft material 32a may include one or more implantable or biocompatible materials having good tensile strength, such as material suitable for resisting expansion when the force associated with blood pressure is applied to it after completion of the stent grafting procedure. For example, the graft material 32a may be made of a woven polyester. In one aspect, the graft material 32a may include collagen, albumin, an absorbable polymer, or biocompatible fiber. In another aspect, the graft material 32a may include one or more metallic, plastic, or non-biodegradable materials. Other graft materials described herein may similarly include one of the aforementioned materials described with respect to graft material 32a.

Wire matrix 32b is shown in dashed lines if it is covered by graft material 32a. Whereas one embodiment of a wire matrix 32b having a zig-zag-type pattern is shown in FIGS. 1a and 1b, other formations and patterns may be used. For example, in some embodiments, the wire matrix 32b may be located only at the proximal and distal ends of the trunk stent 30, while in other embodiments, portions of the wire matrix 32b may be located along the entirety of the length of the body 32. In some embodiments, as shown in FIGS. 1a and 1b, the ends of the wire matrix 32b extend beyond an end of the stent body 32, and further can include hooks 32c for securement of the stent 30 to the arterial wall or lumen (not shown). In some embodiments, stent 30 includes spacing between the end of the wire matrix 32b and the end of the graft material 32a, this unsupported graft material 32a being adapted and configured for increased flexibility and sealing against either the arterial wall, or the graft material of an adjacent stent.

As seen in FIG. 1b, trunk stent 30 may include an aperture 38 located along one side of the cylindrical shape of the body 32. In one aspect, the aperture is surrounded by a lip 38a of graft material 32a that is not coupled to the wire mesh 32b. In some embodiments, aperture 38 may be generally oval in shape, although other embodiments of the present disclosure contemplate an aperture of any shape that permits fluid communication with various branched arteries as described herein. Suitable aperture geometries may include a square, rectangle, circle or polygonal shaped openings. Moreover, a trunk stent 30 may include two or more apertures 38 positioned in the body 32. If more than one aperture 38 is included, the apertures may be positioned in close proximity, such as on the same side of the body 32, or apart from one another, such as in opposing faces of the body 32. In one aspect, the two or more apertures may be spaced circumferentially or longitudinally. In another aspect, the shapes of the apertures 38 may be the same or different. Other shapes, orientations and arrangements for one or more apertures 38 are also possible.

In some embodiments, the body 32 of the trunk stent 30, including the wire matrix 32b or the graft material 32a, may be expandable. For example, a trunk stent 30 may be provided in a contracted state which may be deployed, for example, by a physician into an expanded state. In one aspect, and expandable body 32 may be either balloon expandable or self-expandable, as in the case where the matrix 32b may be made of a shape-memory material. In some embodiments, only a portion of the body 32 is an expandable body, whereas in other embodiments, the entirety of the body 32 may be expandable.

Figure 2B:
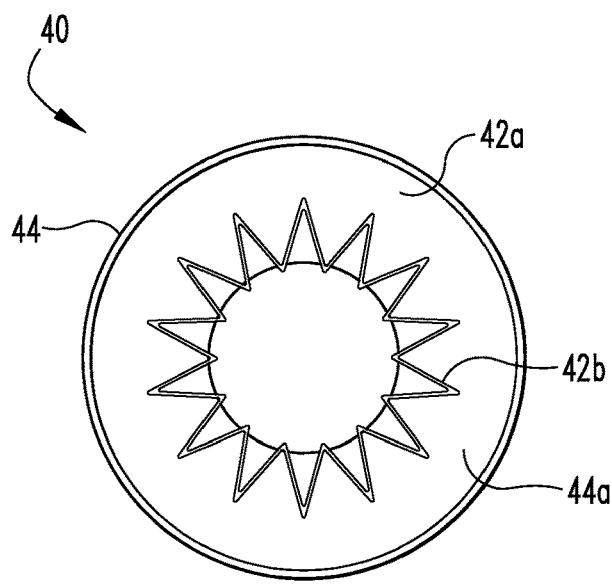
FIG. 2b is a top plan view thereof.

FIGS. 2a and 2b show side and frontal views, respectively, of a trumpet stent 40 according to one embodiment of the present disclosure. Trumpet stent 40 includes a body 42 extending from an open first end or proximal end 44 to an open second end or distal end 46. In one aspect, the Stent body 42 includes a graft material 42a that covers a wire matrix 42b. Wire matrix 42b may be fabricated from a biocompatible, shape-memory material such as Nitinol or a stainless steel. Wire matrix 42b is shown and dashed lines if it is covered by graft material 42a. In some embodiments, the ends of the wire matrix 42b may extend beyond an end of the stent body. In other embodiments, the wire matrix 42b may include hooks 42c for securement of the stent to the arterial wall. In some embodiments, stent 40 includes spacing between the end of the stent matrix and the end of the graft material, this unsupported graft material 44a being adapted and configured for increased flexibility and sealing against the arterial wall, the graft material of an adjacent stent or another surface. In some embodiments, aspects of the construction of trumpet stent 40 may be similar to that of trunk stent 30. For example, trumpet stent 40 may include an expandable body that may be self-expandable or balloon expandable. Moreover, the wire matrix 42b may be located in selected locations along the length of the body 42 such as exclusively at the proximal end 44 and distal end 46 or spaced across a majority of the body 42.

Trumpet stent 40 is shown in FIGS. 2a and 2b in an expanded and free state. A portion of body 42 and distal end 46 may be substantially circular for placement within an interior space of an artery or lumen. Proximal end 44 may have a larger diameter than distal end 46. A portion of body 42 transitions from the generally cylindrical section toward the larger diameter proximal end 44 with a conical type of shape, or a flaring out. While one possible shape is shown for a trumpet stent 40 in FIGS. 2a and 2b, other shapes and configurations may also be used. For example, the proximal end 44 may have a concave outer surface as opposed to the convex surface shown in the Figures. In another aspect, a transverse cross-section of the body 42 may be generally circular as shown in FIG. 2b or it may be another shape, such as an ellipse, square, rectangle or other polygonal or curvilinear shape. Moreover, the transverse cross-section may vary along the length of the body 42. For example, a proximal end 44 of the body 42 may have an elliptical cross-section, while a distal end 46 of the body 42 may have a circular cross section. In some embodiments, the perimeter of the proximal end 44 may be greater than the perimeter of the distal end 46 as. Alternatively, the perimeter of the proximal end 44 may be less than or equal to the perimeter of the distal end 46.

Figure 3:
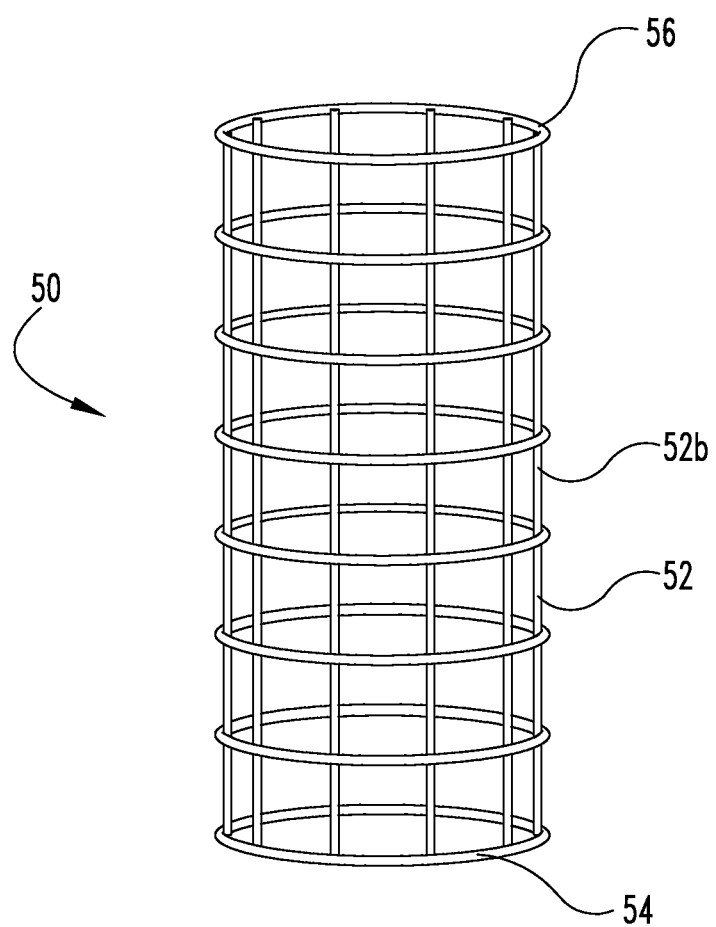
FIG. 3 is a perspective view of a securement stent according to one embodiment of the present disclosure.
Figure 4:
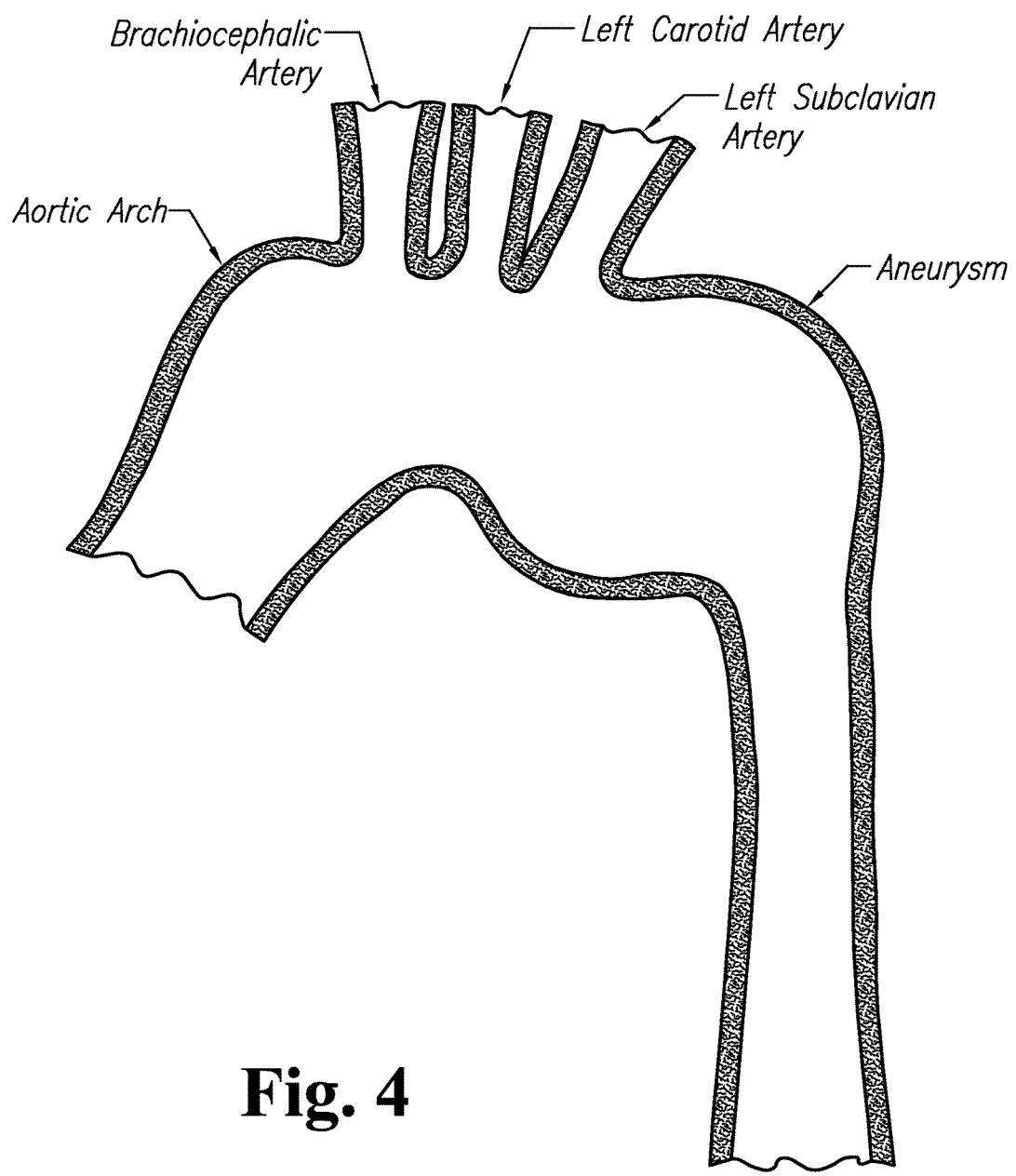
FIG. 4 is a schematic cutaway representation of a region of the upper aorta including a thoracic aortic aneurysm.

FIG. 3 shows side and frontal views, respectively, of a generally cylindrical securement stent 50 according to one embodiment of the present disclosure. Securement stent 50 includes a body 52 extending from a proximal end 54 to a distal end 56. Stent body 52 includes a wire matrix 52b. Wire matrix 52b may be fabricated from a biocompatible, shape-memory material such as Nitinol or a stainless steel.

Securement stent 50 is shown in an expanded and free or unrestricted state in FIG. 3. Accordingly, the body 52 of the securement stent 50 may be an expandable body. As described for trunk stent 30 and trumpet stent 44, securement stent 50 may include a self-expandable or balloon expandable body 52. In the expanded state, the free outer diameter (perimeter) of the wire mesh 52b may be larger than the inner diameter (perimeter) of trunk stent 30. Therefore, when securement stent 50 is deployed inside trunk stent 30 there is compression in the interface between the two stents. In the illustrated embodiment, the length of securement stent 50 from proximal end 54 to distal end 56 is less than the length of trunk stent 30 from proximal end to distal end. In one aspect, the securement stent 50 may be sized to have a length that is at least slightly greater than a longitudinal dimension of the aperture 38 of the trunk stent 30. In other embodiments, the length of the securement stent may be greater than the overall length of the body 32 of the trunk stent 30.

FIGS. 4-10 pertain to the installation of a stent assembly 20 according to one embodiment of the present disclosure. The stent assembly 20 may be deployed proximal to aneurysm located in a portion of the thoracic aorta. In one aspect the portions of the stent assembly 20 may be positioned in the aortic arch with portions of the stent assembly 20 extending into one or more arteries in communication with the aortic arch, such as the brachiocephalic artery, left carotid artery, left subclavian artery, and the like. While FIGS. 4-10 illustrate an embodiments of a stent assembly 30 deployed in one location within the thoracic aorta, embodiments of a stent assembly may be suitably positioned in other arterial spaces or lumens in general.

Figure 5:
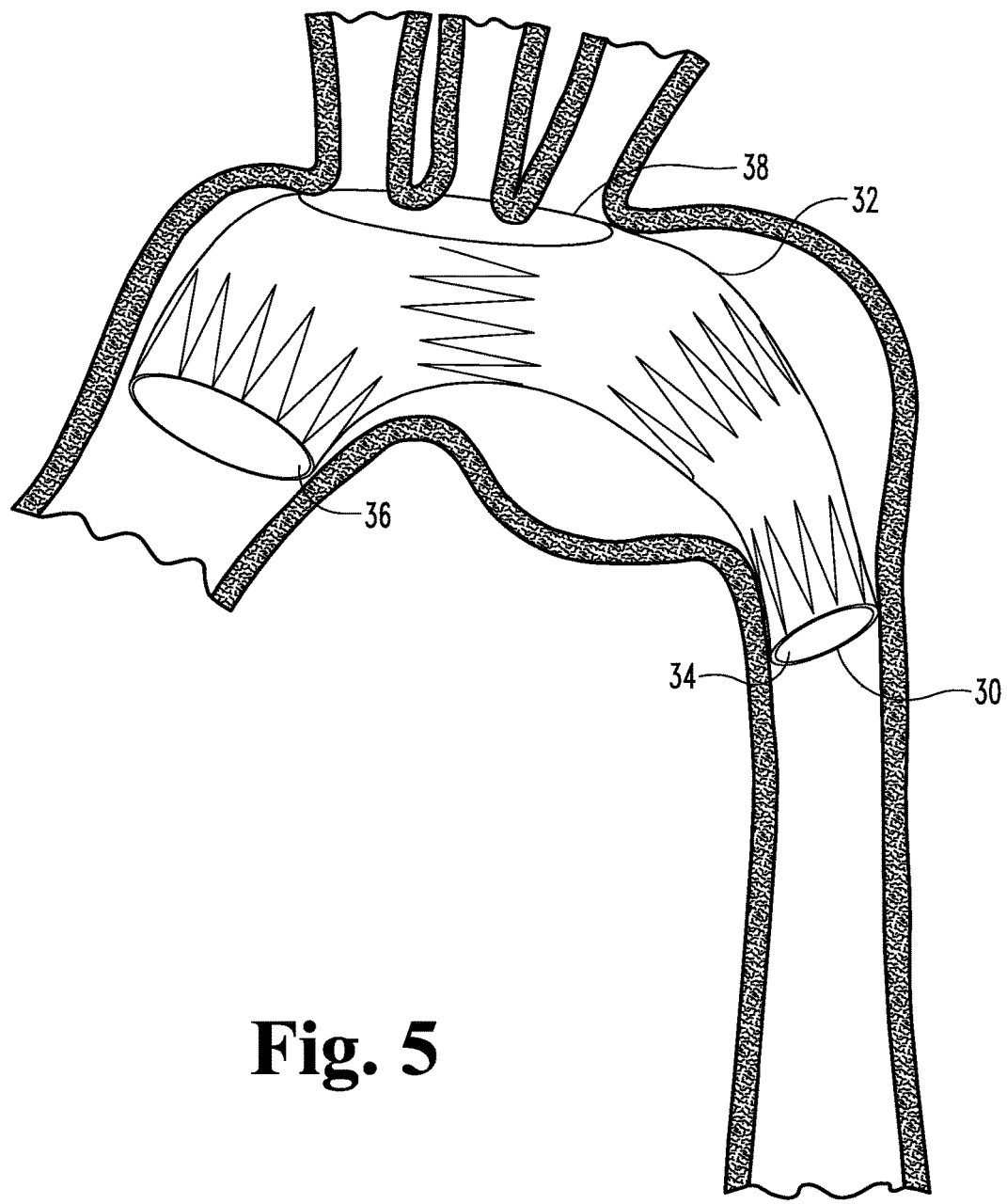
FIG. 5 shows the aorta of FIG. 4 with a trunk stent installed according to one embodiment of the present disclosure.

Turning to FIG. 5, a trunk stent 30 is first deployed within the aortic arch. The length of stent 30 is sufficient to extend between portions of healthy arterial wall, with the aneurysm being located between the proximal and distal ends of stent 30. Stent 30 is oriented within the aortic arch such that central aperture 38 is generally aligned with the brachiocephalic, left carotid, and left subclavian arteries. With such placement, the interior of stent 30 may be in fluid communication with these three arteries by way of central aperture 38. The aperture 38 (or one or more additional apertures) may in addition (or alternatively) be in fluid communication with other arteries, for example, depending up the size and location of the aneurysm.

Figure 6:
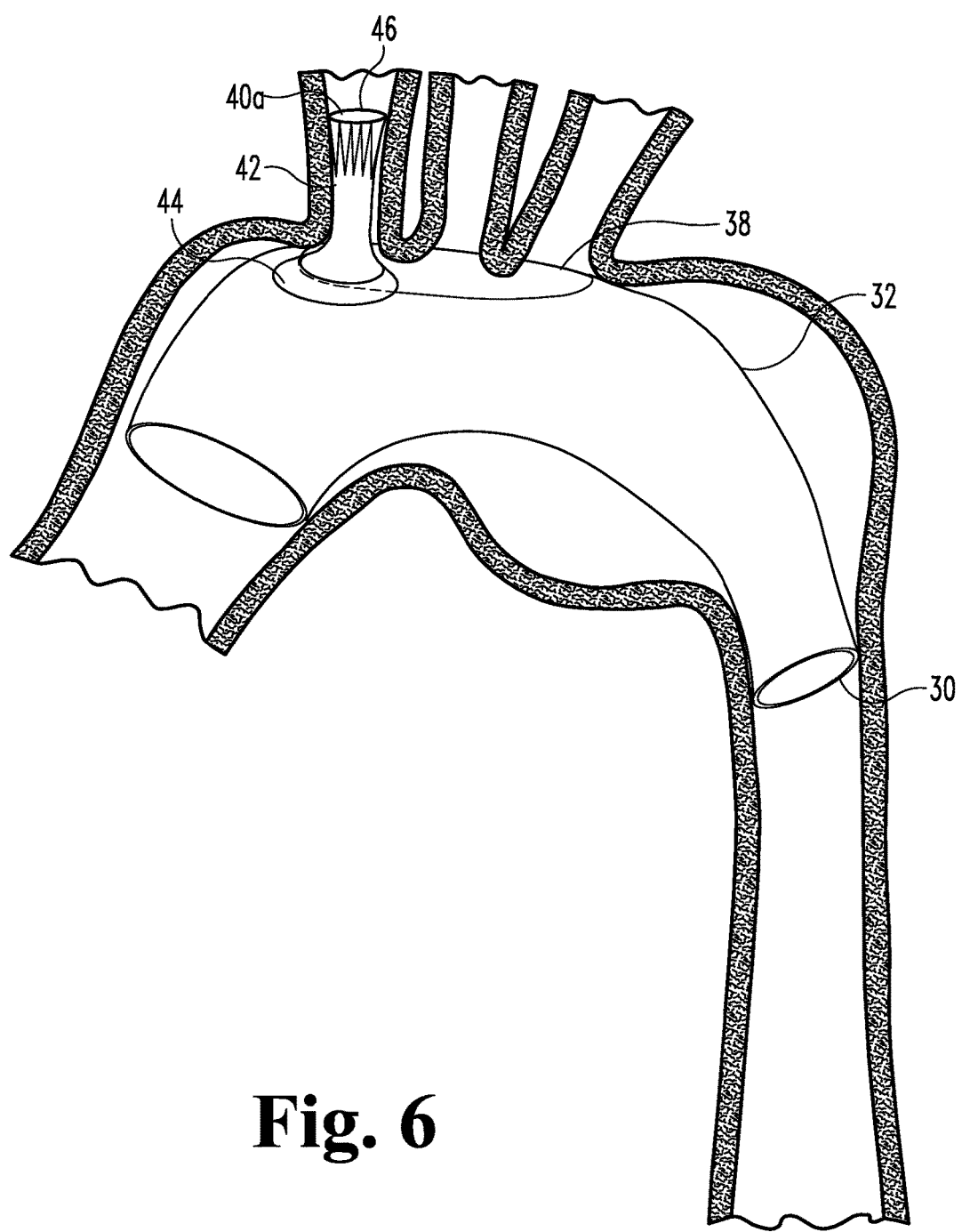
FIG. 6 shows the aorta of FIG. 5 with a first trumpet stent installed according to one embodiment of the present disclosure.
Figure 7:
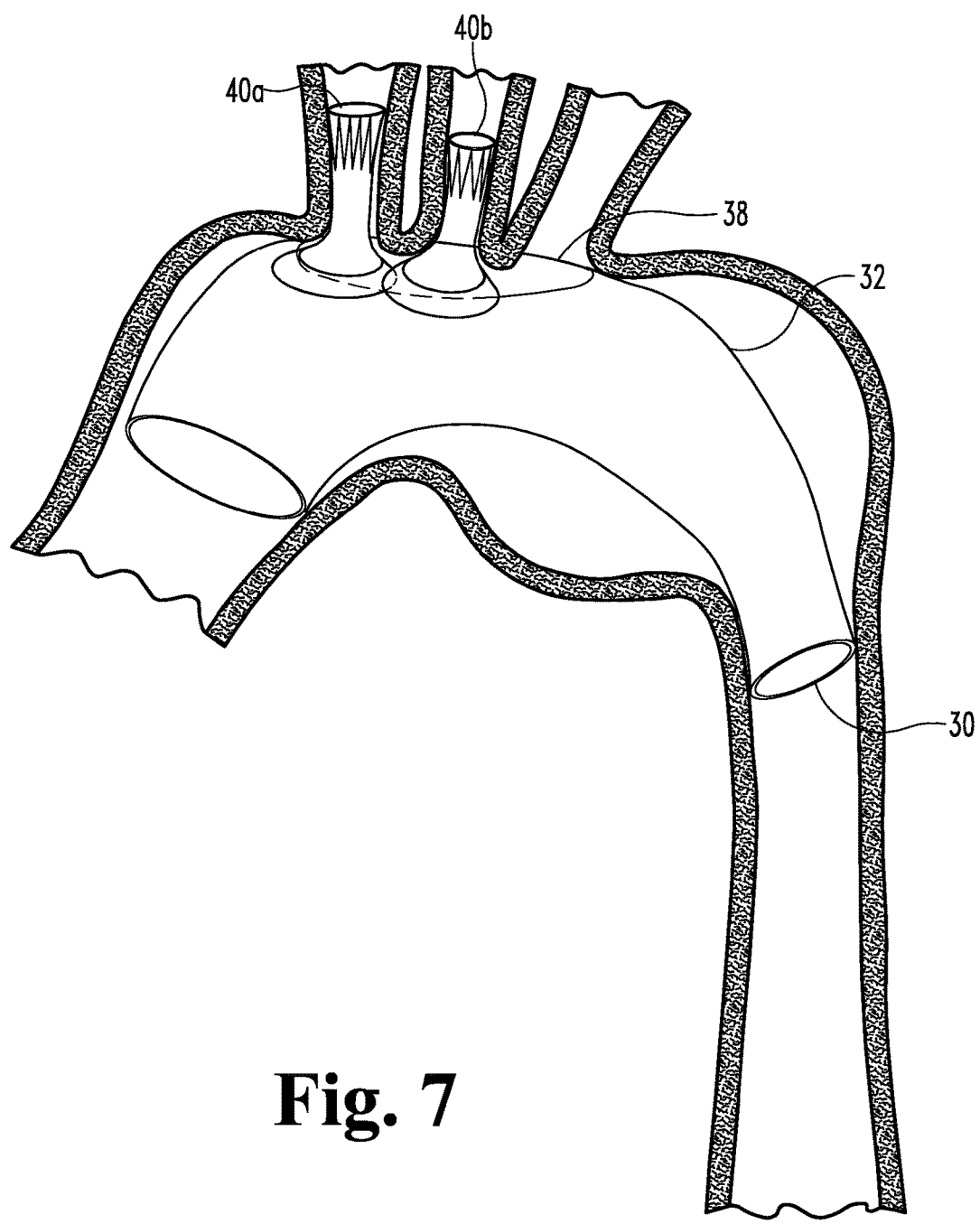
FIG. 7 shows the aorta of FIG. 6 with a second trumpet stent installed according to one embodiment of the present disclosure.
Figure 8:
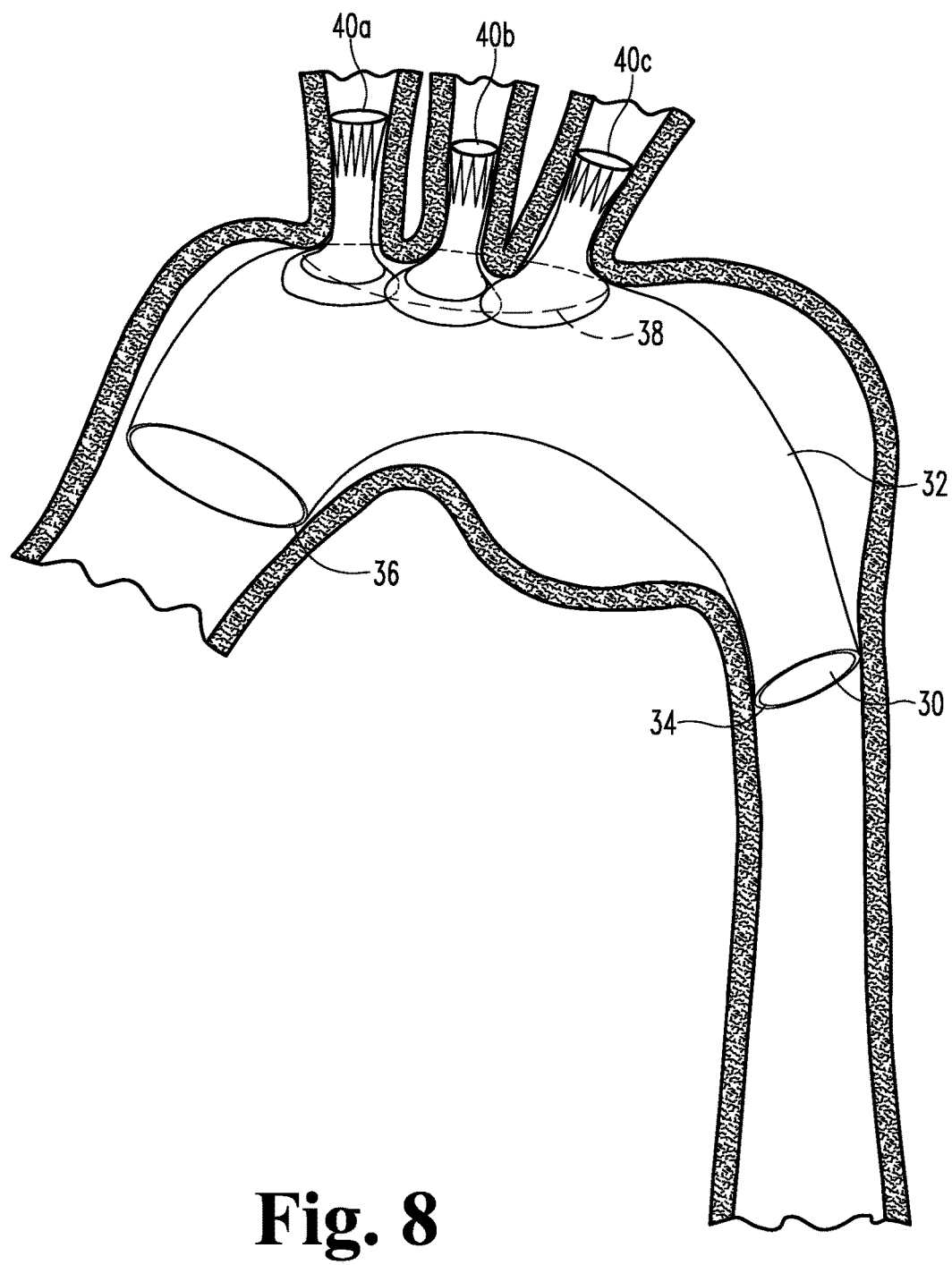
FIG. 8 shows the aorta of FIG. 7 with a third trumpet stent installed according to one embodiment of the present disclosure.

FIG. 6 shows a first trumpet stent 40a in the deployed state. The cylindrical portion of stent body 42a extends within the brachiocephalic artery. In one aspect, the body 42 of the trumpet stent 40 passes through the aperture 38 of the trunk stent 30 such that the first or proximal end 44 of the trumpet stent 40 is positioned at least partially within the interior space of the trunk stent 30. In one aspect, the flaring portion of trumpet stent 40a extends through aperture 38 into the central volume of trunk stent 30. A portion of the distal lip 44a overlaps a portion of the lip 38a surrounding aperture 38. A different, interior portion of lip 44a extends under the arterial wall between the brachiocephalic and left carotid arteries, and does not overlap with body 32 of trunk stent 30. FIGS. 7 and 8 show the deployment of second and third trumpet stents 40b and 40c. In each case, a portion of the flaring proximal end of the stent overlaps a portion of the lip 38a surrounding central aperture 38. Further, yet other portions of the flaring proximal ends overlap the flaring proximal end of the adjacent trumpet stent.

Figure 9:
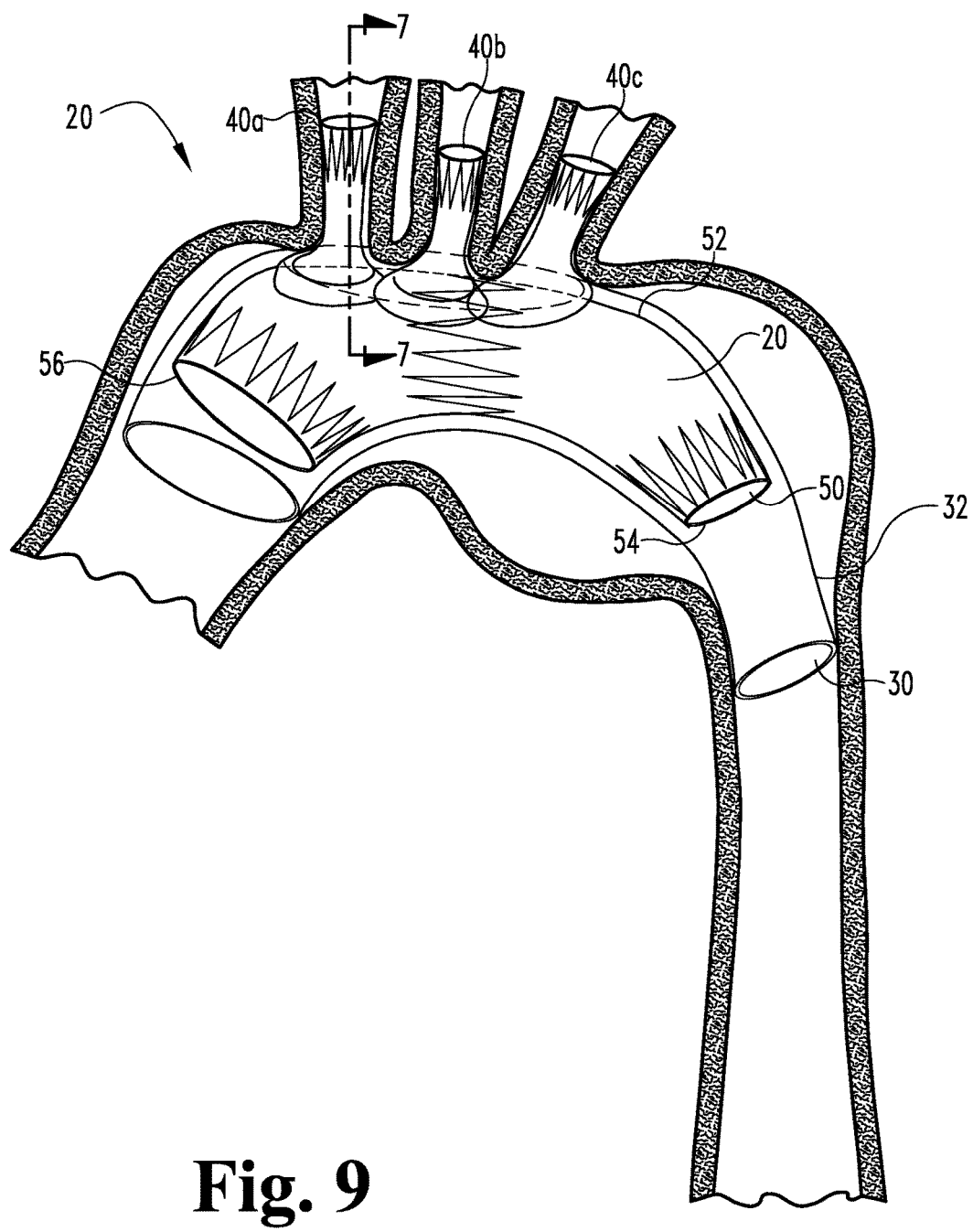
FIG. 9 shows the aorta of FIG. 8 with a securement stent installed according to one embodiment of the present disclosure.

FIG. 9 shows the deployment of securement stent 50 within the interior of trunk stent 30. As discussed previously, when deployed, stent 50 may expand to achieve an outer diameter slightly larger than the inner diameter of trunk stent 30. Therefore, the outer surface of body 52 is generally compressed against the inner surface of body 32. In addition, a portion of body 52 presses against the three flared proximal ends 44a, 44b, and 44c. In some embodiments securement stent 50 does not include any grafting material. Therefore, body 52 may not cover the internal passageways of the three trumpet stents that are in fluid communication with their corresponding arteries.

Figure 10:
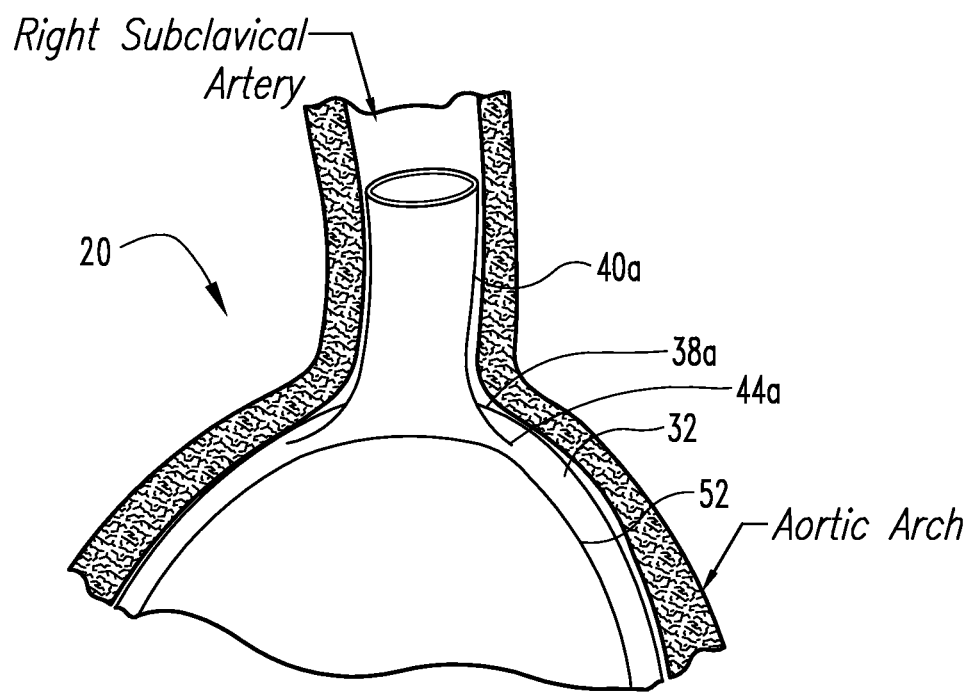
FIG. 10 is a cutaway of a portion of FIG. 9 as taken along line 10-10 of FIG. 9.

FIG. 10 shows a cross section of the juncture of the trunk, trumpet, and securement stents. A flared lip 44a of stent 40a extends past the edge of aperture 38, and overlaps with the graft material 38a that generally surrounds aperture 38. Securement stent 50 compresses against body 32, such that lip 44a is "sandwiched" between bodies 52 and 32.

While one embodiment of a stent assembly 20 is shown in FIG. 9, other embodiments of stent assemblies can be constructed in varying configurations with one or more additional parts and with other parts optionally removed. For example, a stent assembly may include only one trumpet stent, more than three trumpet stents, or no trumpet stents at all. If more than one trumpet stent is included in a stent assembly, the body of each trumpet stent may pass through the same or different apertures in a trunk stent. In one aspect, a first trumpet stent may include an aperture through which a second trumpet stent (or another stent type) may pass for coupling with the first trumpet stent. Moreover, the order in which the stent assembly may be constructed may vary, for example, depending on the location of deployment, the number of components, the type of components (e.g., trumpet stent vs. trunk stent), and the like.

Turning now to FIGS. 11-18, another embodiment of a modular stent assembly 120 including an open body stent design is shown. In particular, FIGS. 11a, 11b, and 11c show an open body stent (stent portion) 60 according to one embodiment of the present disclosure. Stent 60 includes a body 62 extending from a proximal end 64 to a distal end 66. Stent body 62 includes a graft material 62a that covers a wire matrix 62b. Wire matrix 62b may be fabricated from a biocompatible, shape-memory material such as Nitinol or a stainless steel. Wire matrix 62b is shown and dashed lines if it is covered by graft material 62a. In some embodiments, the ends of the wire matrix 62b extend beyond an end of the stent body, and further can include hooks 62c for securement of the stent to the arterial wall. In some embodiments, stent 60 includes spacing between the end of the stent matrix and the end of the graft material, this unsupported graft material being adapted and configured for increased flexibility and sealing against either the arterial wall, or the graft material of an adjacent stent.

Stent 60 includes a generally cylindrical arm 68 that may be adapted or configured to be received within the lumen of an artery, such as a renal artery. Arm 68 may have a configuration similar to that of body 62, and includes a wire mesh latticework 62b attached to and supporting graft material. Moreover, arm 68 may be aligned with an aperture 69 formed in body 62. Stent 60 has a body 62 that may not define a closed shape such as a cylinder. In some embodiments, body 62 is characterized by a sheet having an incomplete annular profile. For example, with reference to FIG. 11c, body 62 includes a first wall 62d extending in a cylindrical arc on one side of arm 68 and second wall 62e extending in substantially the same manner on the other side of arm 68. The walls 62d and 62e each include a free longitudinally-oriented edge. The walls 62d and 62e are adapted and configured to fit within a particular lumen such that when deployed, there is an included angle $\alpha_1$ between the free edges that may be greater than about 90 degrees.

Figures 12A, 12B, 12C:
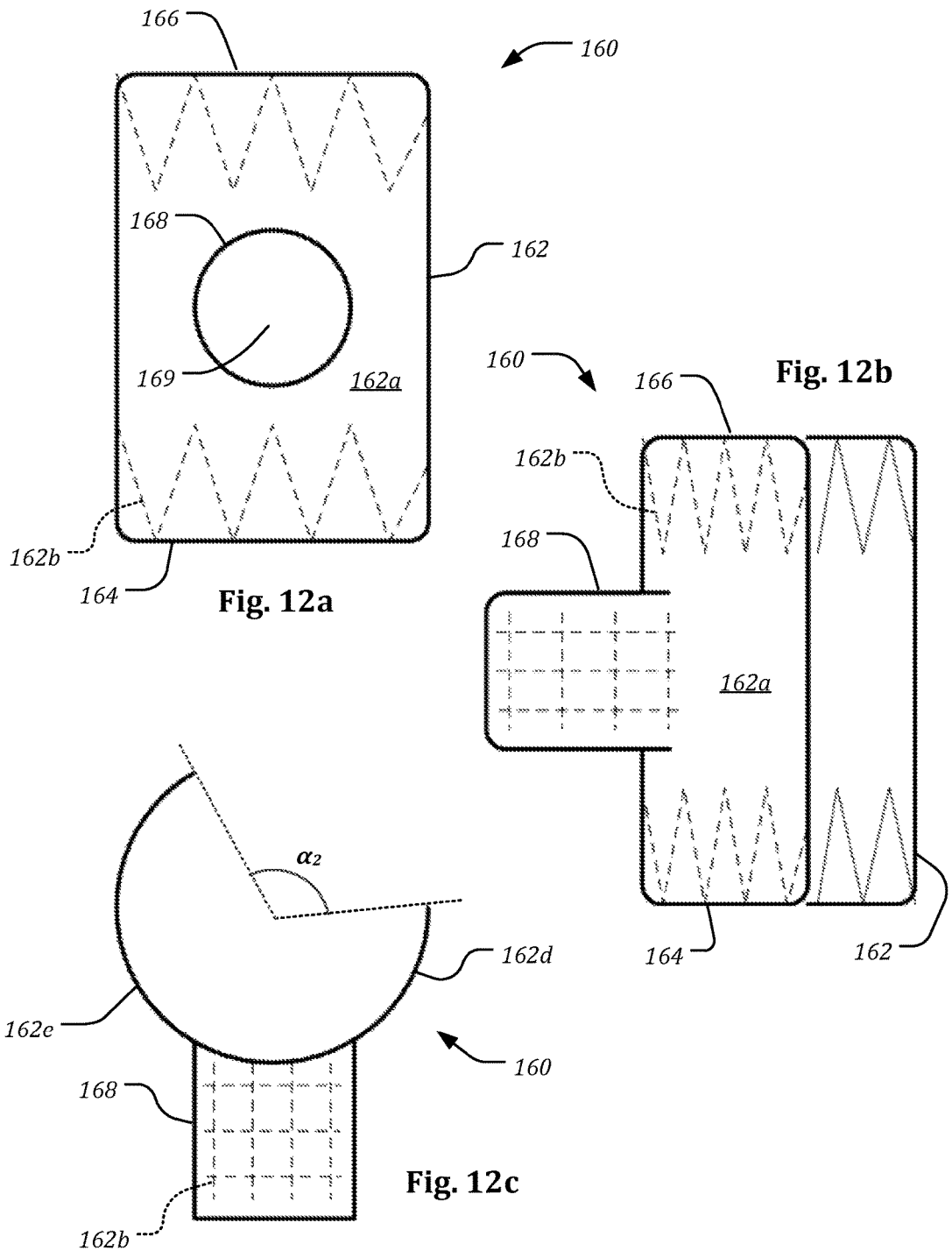
FIG. 12a is a front elevational schematic representation of a modular open body stent according to another embodiment of the present disclosure.
FIG. 12b is a side elevational view thereof.
FIG. 12c is a top plan view thereof.

FIGS. 12a, 12b, and 12c show side and frontal views, respectively, of an open body stent (stent portion) 160 according to one embodiment of the present disclosure. Stent 160 includes a body 162 extending from a proximal end 164 to a distal end 166 and an arm 168 aligned with an aperture 169 in body 162. In one aspect, stent body 162 includes a graft material 162a that covers a wire matrix 162b. Wire matrix 162b may be fabricated from a biocompatible, shape-memory material such as Nitinol or a stainless steel. Wire matrix 162b is shown and dashed lines if it is covered by graft material 162a. In some embodiments, the ends of the wire matrix 162b extend beyond an end of the stent body, and further can include hooks 162c for securement of the stent to the arterial wall. In some embodiments, stent 160 includes spacing between the end of the stent matrix and the end of the graft material, this unsupported graft material being adapted and configured for increased flexibility and sealing against either the arterial wall, the graft material of an adjacent stent, and the like.

As seen in FIG. 12c, stent 160 may be similar to stent 60, except that in one aspect, walls 162d and 162e may not be symmetric or of the same width. In the illustrated embodiment, wall 162d has a shorter width or extent than wall 162e. In some embodiments, the included angle 162f between the free edges (as installed in a generally cylindrical lumen) is greater than about 90 degrees.

With respect to open body stents or stent portions 60 and 160, one or more features may be varied from the illustrated embodiments. For example, body 62 may include portions of wire matrix 62b located only at the proximal end 64 and distal end 66. Instead (or in addition), wire matrix 62b may be located only at one end of the body 62, at intermediate locations across the body 62, or around a perimeter of the body 62. Other wire matrix 62b configurations may also be used. In another aspect, the graft material 62a may entirely cover the wire matrix 62b or portions of the wire matrix 62b may remain exposed. Moreover, the graft material 62a and wire matrix 62b included in the body 62 may be the same or different from the graft material and wire matrix used for the cylindrical arm 68.

In another aspect, the location of the arm 68 may vary. For example, the arm 68 may be positioned centrally with respect to body 62 as in FIG. 11a, or arm 68 may have an offset position, such as towards a longitudinal edge of wall 62d or wall 62e, or a proximal end 64 or distal end 66 of the body 62. In some embodiments, either or both of arm 68 and aperture 69 may be omitted from a stent portion 60. In other embodiments, the shape of aperture 69 and the profile of arm 68 may vary. In one example, the aperture 69 may be rectangular while the arm 68 may have a circular profile.

In some embodiments, the body 62 or arm 68 may of stent 60 may be an expandable body. For example, one or both of body 62 and arm 68 may be self expandable or balloon expandable. In other embodiments, when expanded within an arterial space or lumen, the walls 62d and 62e may generally have a partial annular profile. When viewed along a longitudinal axis of the stent 60 as in FIG. 11c, the walls 62d and 62e may define a partial perimeter of a circular area. The angle $\alpha_1$, defined by center point of the circular area and the endpoints (i.e., longitudinal edges) of the walls 62d and 62e, may vary from less than about 30 degrees to greater than about 270 degrees, for example, depending on the configuration of the modular stent assembly 120. Whereas one embodiment is described with an angle $\alpha_1$ greater than about 90 degrees, other larger or smaller angles may be used. Moreover, when two or more stent portions are assembled to at least partially provide a modular stent assembly, the angles and dimensions of the walls may vary between stent portions. It will be appreciated that the aforementioned features as applied to stent 60 may also apply to stent 68 and portions of a modular stent assembly in general.

Figure 13:
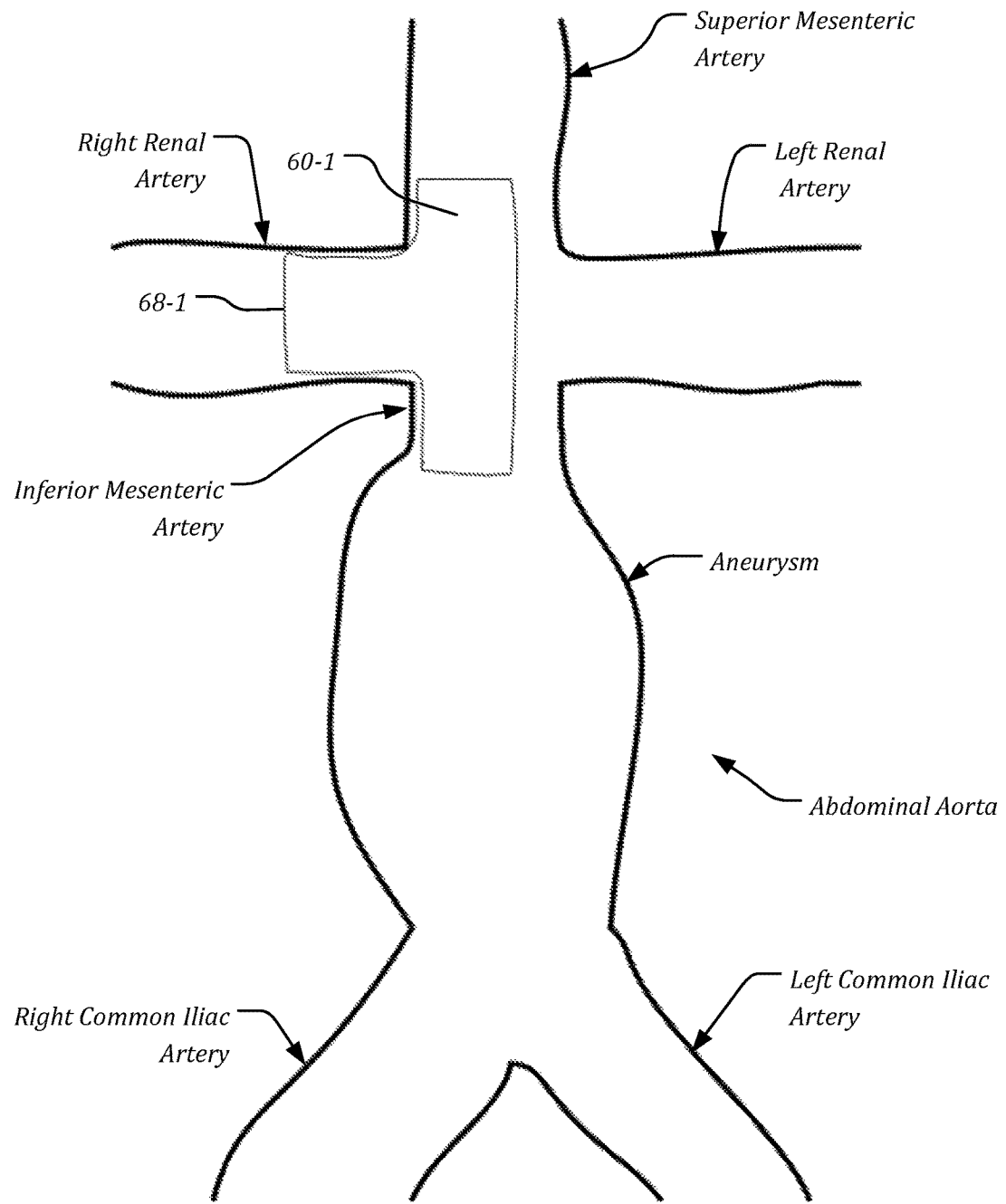

Referring to FIG. 13, a first stent 60-1 is shown deployed between the superior and inferior mesenteric arteries. The arm 68-1 extends within a first (right) one of the renal arteries. The open side (and free edges) of stent body 62 are oriented open toward the second (left) renal artery.

Figure 14:
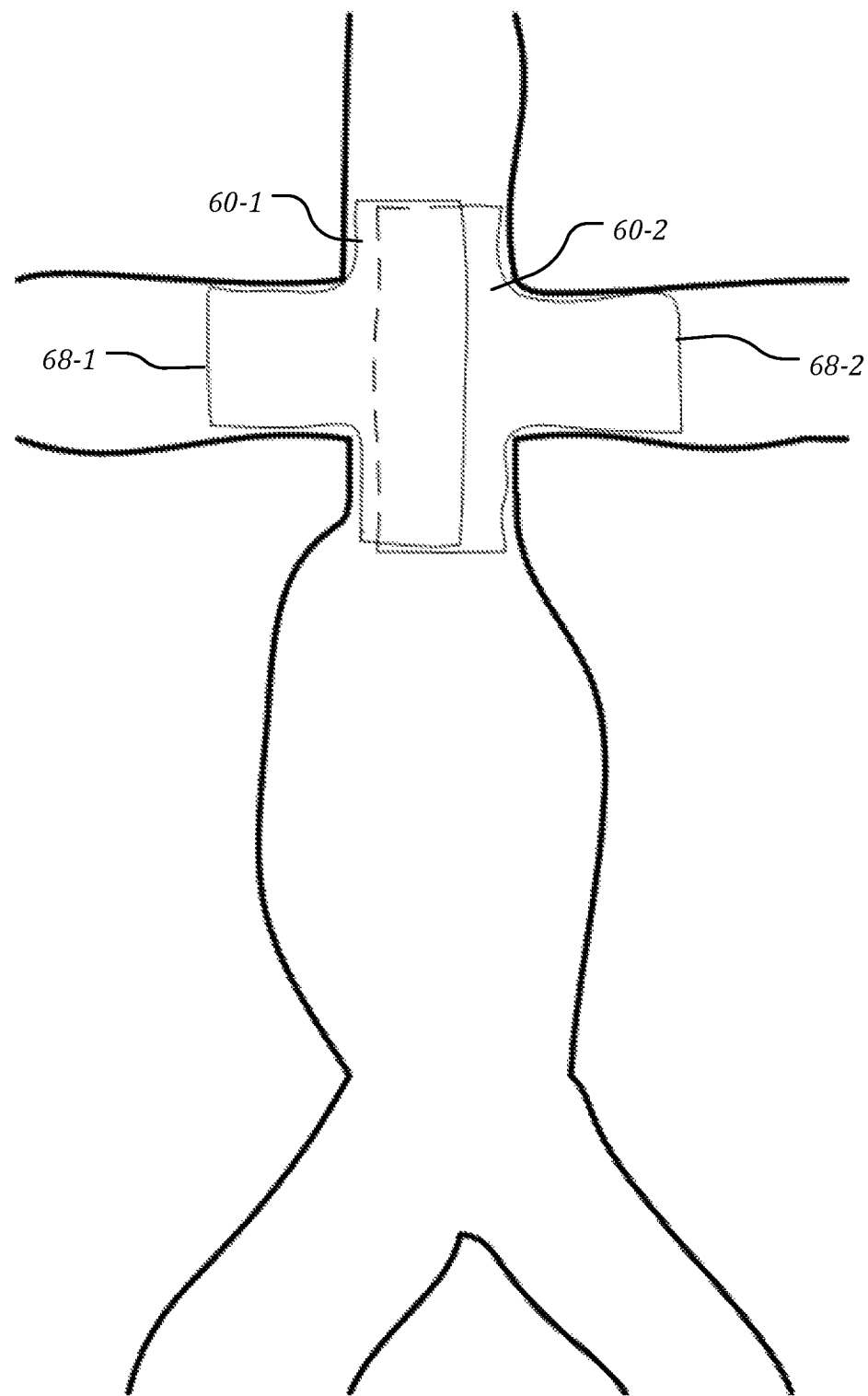

FIG. 14 shows a second stent 60-2 also placed between the superior and inferior mesenteric arteries. The central aperture 68-2 extends within the second (left) renal artery. The opened portion of body 62-2 (and the free edges thereof) is oriented open toward the first (right) renal artery. When both stents are deployed, wall 62d-1 overlaps at least partially with wall 62e-2. Likewise, wall 62e-1 overlaps at least partially with wall 62d-2. This overlapping region can be seen spanning beyond the diameter of the lumens of the renal arteries. Since the stents 60-1 and 60-2 are located within the mesenteric artery by the location of the corresponding renal lumen, it is possible that the proximal and distal ends of the two stents do not coincide, but rather can be offset slightly.

Figure 15:
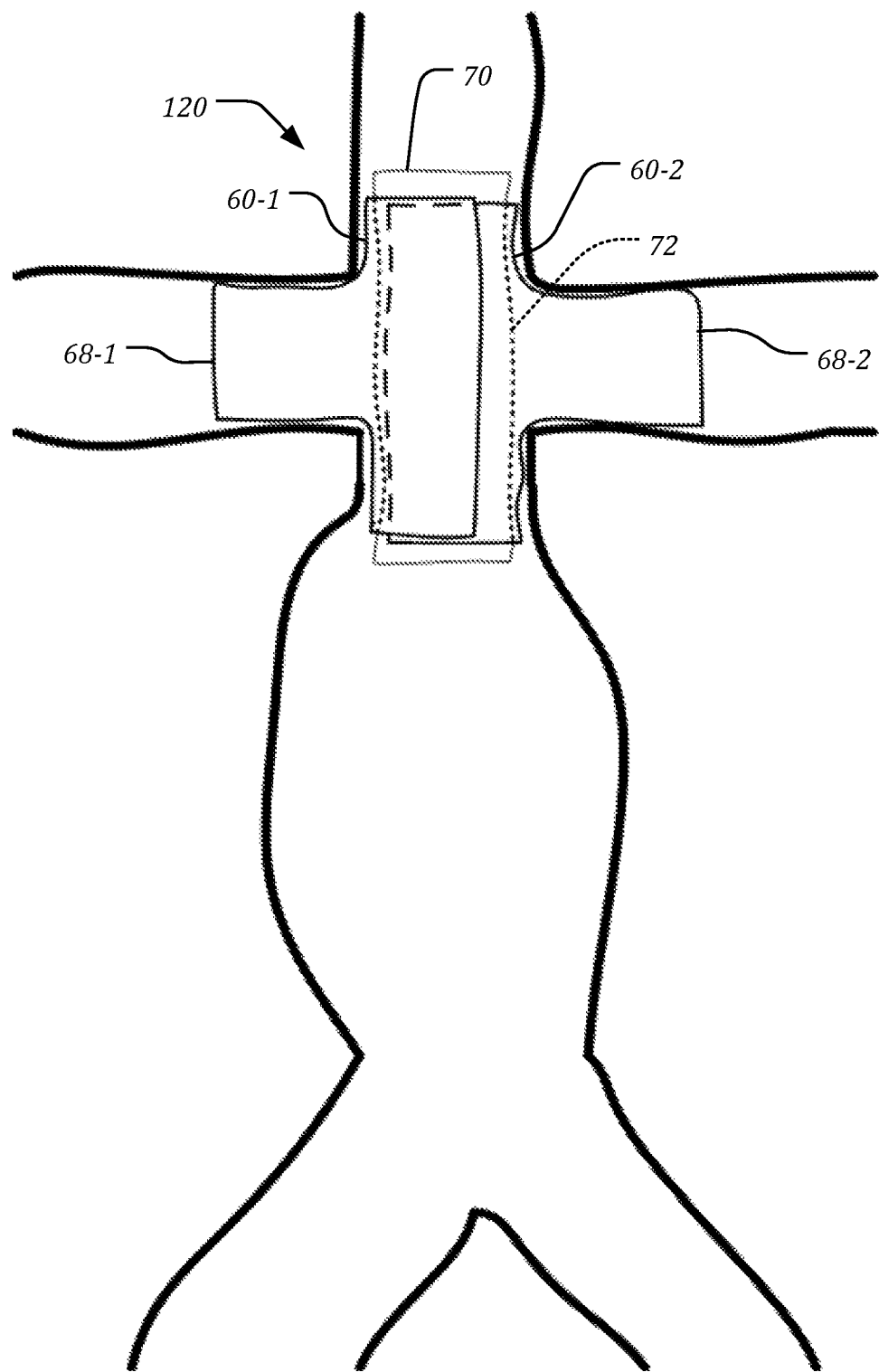
FIG. 15 is a schematic cutaway representation of the abdominal aorta of FIG. 14 further including an installed securement stent such as the one shown in FIG. 3.

FIG. 15 shows a securement stent 70 deployed within both bodies 62-1 and 62-2. Similar to securement stent 50, securement stent 70 is sized so as to deploy to a diameter that places the stent walls 62-1 and 62-2 in compression against each other, and further in compression against the lumen wall. The assembly of stents 60-1, 60-2, and 70 comprises a stent assembly 120 according to another embodiment of the present disclosure. Further discussion of embodiments of a modular stent assembly will be made relative to FIG. 18.

Figure 16:
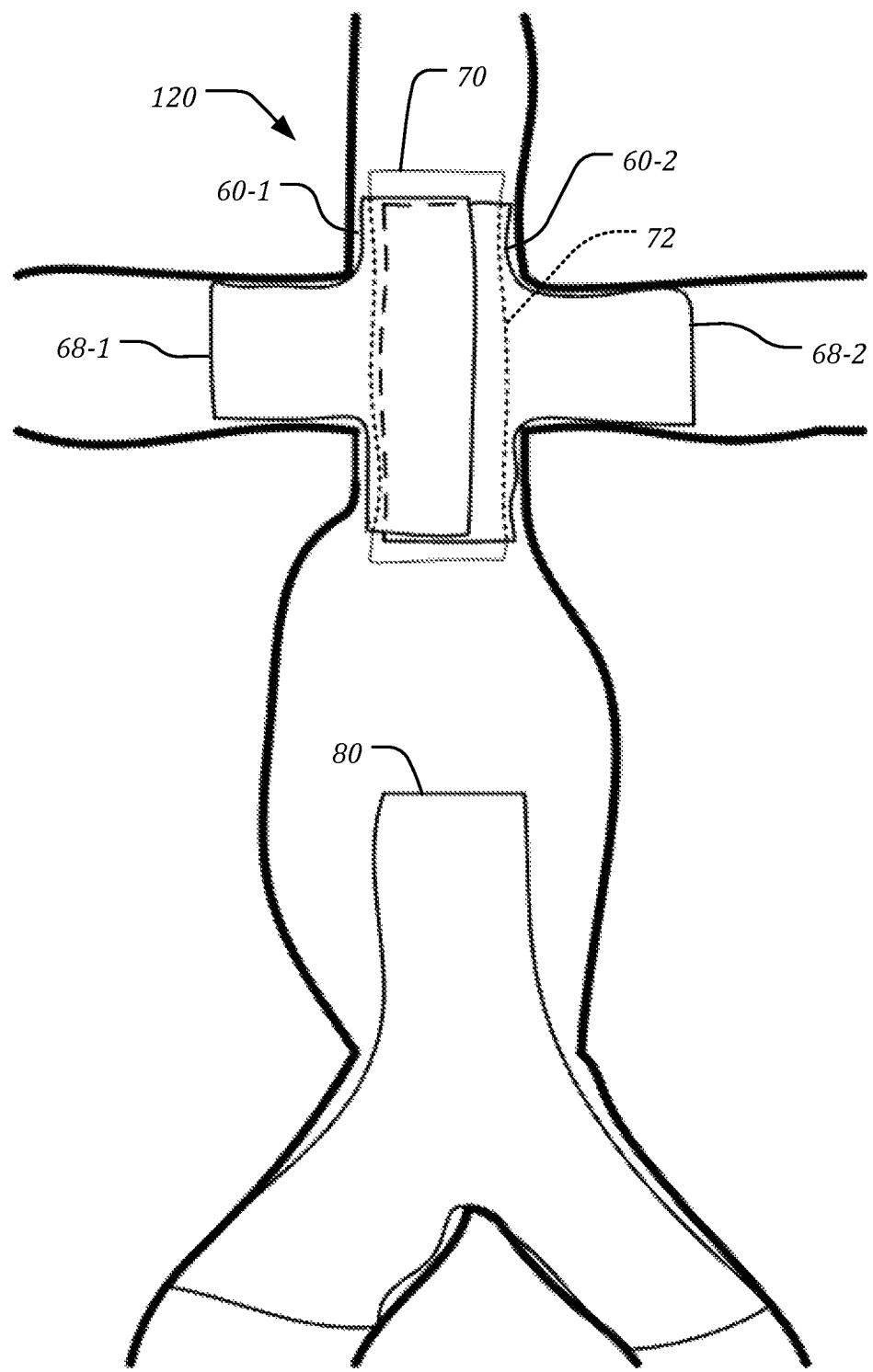
FIG. 16 is a schematic cutaway representation of the abdominal aorta of FIG. 15 further including an installed bifurcated stent.
Figure 17:
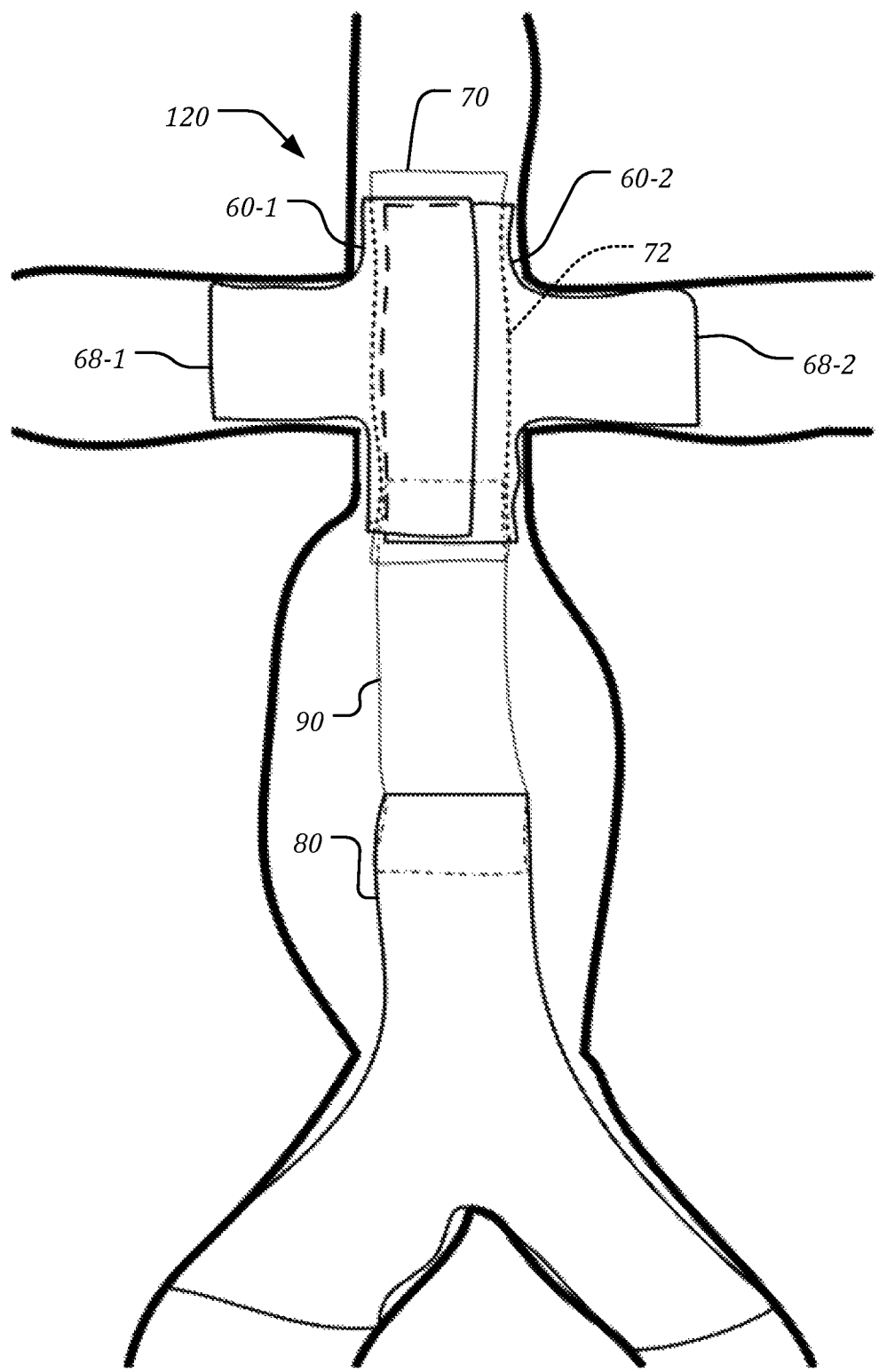
FIG. 17 is a schematic cutaway representation of the abdominal aorta of FIG. 16 further including an installed overlapping stent.

FIGS. 16 and 17 show yet another embodiment of the present disclosure in which stent assembly 120 is used as a secured site for attachment to other stents that address the patient's aneurysm. Referring to FIG. 16, a bifurcated stent 80 includes branches located within each of the iliac arteries. A central trunk of stent 80 extends within the inferior mesenteric artery into the region having the aneurysm. FIG. 17 shows a second, coupling stent 90 that is deployed to achieve fluid communication from stent assembly 120 to bifurcated stent 80. Stent 90 overlaps with both securement stent 70 and the central trunk of bifurcated stent 80.

Figure 18A:
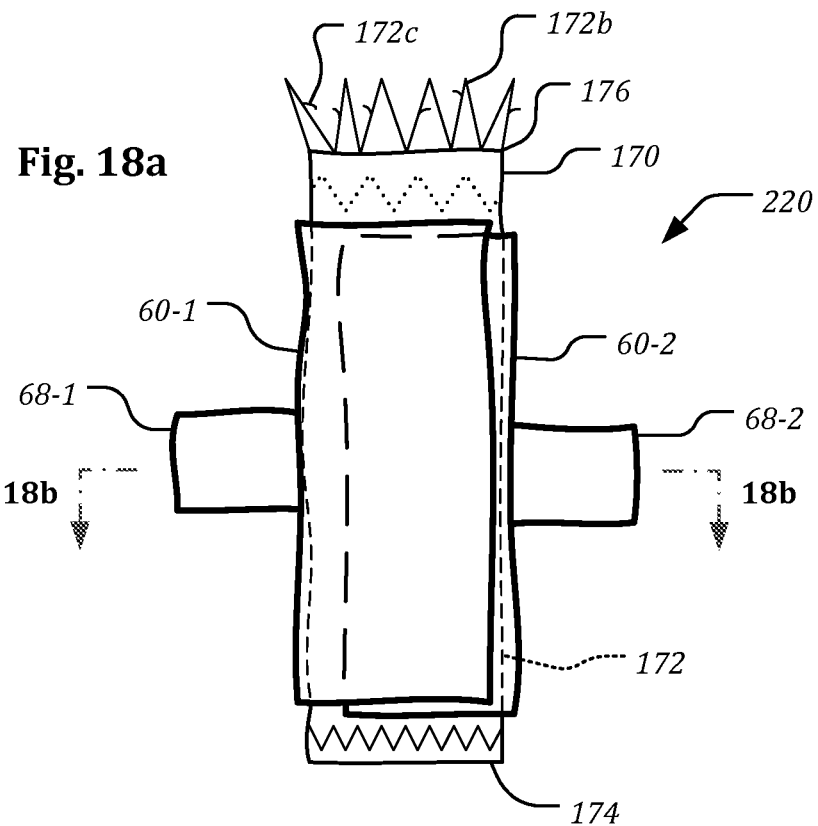
FIG. 18a is a side elevational view of a modular stent assembly according to one embodiment of the present disclosure.
Figure 18B:
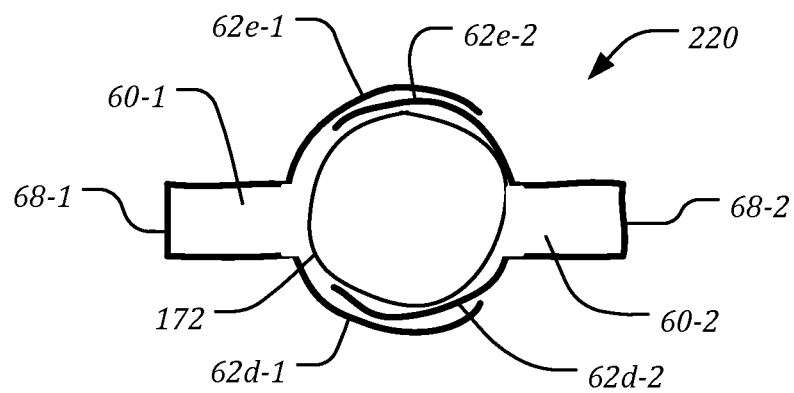

FIGS. 18a and 18b show views of an embodiment of a securement stent 170 according to one embodiment of a modular stent assembly 220. Securement stent 170 includes a body 172 extending from a proximal end 174 to a distal end 176. Stent body 172 includes a graft material 172a that covers limited portions of a wire matrix 172b. Wire matrix 172b may be fabricated from a biocompatible, shape-memory material such as nitinol or a stainless steel. Wire matrix 172b is shown and dashed lines if it is covered by graft material 172a. In some embodiments, the ends of the wire matrix 172b extend beyond an end of the stent body 172, and may include hooks 172c for securement of the stent to the arterial wall. In some embodiments, stent 170 may include spacing between the end of the stent matrix 172b and the end of the graft material 172a, this unsupported graft material 172a being adapted and configured for increased flexibility and sealing against either the arterial wall, the graft material of an adjacent stent, and the like.

Securement stent 170 includes a distal end 176 having a portion of wire mesh 172b that extends out past graft material 172a. In some embodiments, a plurality of hooks 172c is incorporated for improved securement of stent 170 to the arterial wall. In one aspect, graft material 172a may extend for limited portions of body 172 near one or both of the proximal end 176 and distal end 174. These limited portions of graft material 172a may provide improved sealing against the inner surfaces of body 62-1 and body 62-2. Further, the graft material proximate to proximal end 174 may provide a sealing surface against the distal end of stent 90 as in FIG. 17. However, the central portion of body 172 may not be covered with a graft material, so as to not impede fluid flow into the renal arteries.

FIG. 18b shows a cross section of modular stent assembly 220, showing the partial overlap of the stent wall 62d-1 with wall 62d-2, and wall 62e-1 with wall 62e-2. From FIG. 18b, it may be seen the wall 62d-2 is positioned between securement stent wall 172, and wall 62d-1. Similarly, 62e-2 is positioned between securement stent wall 172, and wall 62e-1. Stent portions 60-1 and 60-2 may be similar in construction to stent portion 60 as shown in FIGS. 11, including generally symmetric walls (e.g., 62d-1 and wall 62d-2). Accordingly, arm 68-1 is aligned and diametrically opposed to arm 68-2.

Figure 18C:
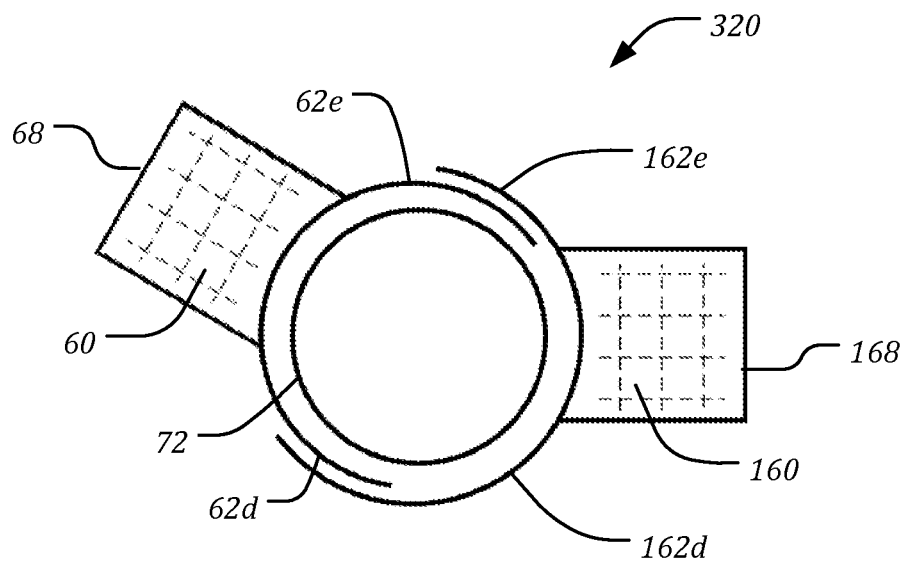
FIG. 18c is a view of a stent assembly similar to that of FIG. 18b, except according to yet another embodiment of the present disclosure.
Figure 18D:
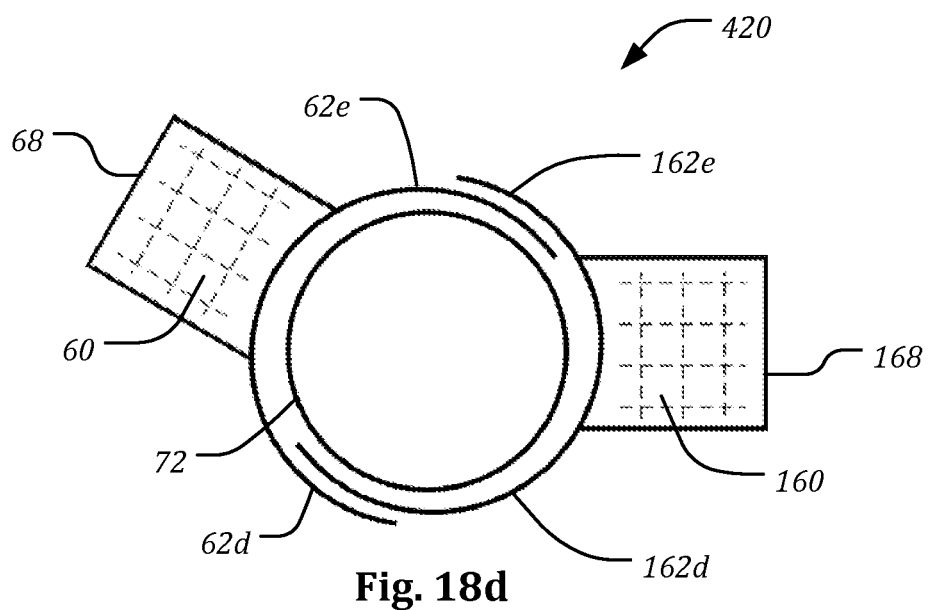
FIG. 18d is a view of a stent assembly similar to that of FIG. 18b, except according to still another embodiment of the present disclosure.

FIGS. 18c and 18d show top views taken along the longitudinal axis of alternative modular stent assemblies 320 and 420, respectively. Assembly 320 in FIG. 18c includes a symmetric stent 60 and an asymmetric stents 160. Symmetric and asymmetric stent portions may be combined, for example, for deployment in a patient having renal arteries best served by an angular offset between the renal artery flow paths. Wall 62d is shown to be positioned between securement stent 72 and wall 162d, while wall 62e is shown to be positioned between securement stent 72 and wall 162e. Accordingly, stent portion 60 is nested within stent portion 160, with securement stent 72 positioned therebetween. When stent portion 60 is assembled with stent portion 160, arm 68 is not aligned or diametrically opposed with arm 168 as in the case of assembly 220. Conversely, arm 68 is positioned at angle that is less than (or greater than) 180 degrees relative to arm 168. In one aspect, the angle between arm 68 and arm 168 may vary to suit the particular geometry of the arterial space or other intersection. Moreover, the walls of each of the stent portions (e.g., walls 62d and 62e of stent portion 60) may vary to achieve a given alignment while still providing at least a partial overlap between corresponding walls.

With reference to FIG. 18d, an alternative embodiment of a modular stent assembly 420 is shown. One difference between assembly 320 and assembly 420 is that stent portion 60 is staggered with stent portion 160 in assembly 420. More particularly, whereas wall 62e is positioned between securement stent 72 and wall 162e as in assembly 320, wall 162d is positioned between securement stent 72 and wall 62d, which differs from assembly 320. As with assembly 320, aspects of assembly 420 may be varied in order to achieve a given angle between arms or wall overlap.

While embodiments of a modular stent assembly have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A modular stent assembly for deployment within a lumen, the modular stent assembly comprising:
   a trunk stent including:
      an expandable body defining an interior space, the body extending between an open proximal end and an open distal end;
      a graft material disposed on the body;
      an aperture positioned between the proximal end and the distal end, the aperture being formed through the body and the graft material;
   a trumpet stent including:
      an expandable body extending between an open first end and an open second end, an outer perimeter of the first end being greater than an outer perimeter of the second end, the trumpet stent further including a flared lip having a gradually increasing diameter;
      a graft material disposed on the body; and
   a securement stent including an expandable body extending between an open proximal end and an open distal end of the securement stent,
   wherein the body of the trumpet stent passes through the aperture of the trunk stent, the first end of the trumpet stent positioned at least partially within the interior space of the trunk stent,
   wherein the securement stent is positioned within the interior space of the trunk stent, and
   wherein an outer wall of the securement stent contacts an inner wall of the trunk stent and the first end of the trumpet stent, sandwiching the flared lip of the trumpet stent between the securement stent and the trunk stent, thereby coupling the trumpet stent to the trunk stent.

2. The modular stent assembly of claim 1, wherein at least one of the trunk stent, the trumpet stent and the securement stent includes a biocompatible, shape-memory material.

3. The modular stent assembly of claim 2, wherein the material is selected from nitinol and stainless steel.

4. The modular stent assembly of claim 1, wherein the second end of the trumpet stent is in fluid communication with the proximal end and the distal end of the trunk stent.

5. The modular stent assembly of claim 1, wherein the expandable body of at least one of the trunk stent, the trumpet stent and the securement stent is balloon expandable.

6. The modular stent assembly of claim 1, wherein the expandable body of at least one of the trunk stent, the trumpet stent and the securement stent is self-expanding.

7. The modular stent assembly of claim 1, wherein at least a portion of the graft material disposed on the body of the trunk stent extends partially over the aperture in the body of the trunk stent.

8. The modular stent assembly of claim 1, wherein at least a portion of the graft material disposed on the body of the trumpet stent extends partially past the first end of the body of the trumpet stent.

9. The modular stent assembly of claim 1, wherein the trumpet stent is a first trumpet stent, and which includes a second trumpet stent, and wherein (i) the second trumpet stent includes an expandable body extending between an open first end and an open second end, (ii) the body of each of the first and second trumpet stents passes through the aperture of the trunk stent, and (iii) the first end of each of the first and second trumpet stents is positioned at least partially within the interior space of the trunk stent.

\* \* \* \* \*